(12) United States Patent
Weaver et al.

(10) Patent No.: US 9,540,667 B2
(45) Date of Patent: Jan. 10, 2017

(54) METHODS OF BIOSYNTHESIZING BACTERIAL EXTRACELLULAR GALACTOMANNAN POLYSACCHARIDES AND SUBUNITS THEREOF FOR USE IN SUBTERRANEAN FORMATION OPERATIONS

(71) Applicant: Halliburton Energy Services, Inc., Houston, TX (US)

(72) Inventors: Jimmie D. Weaver, Duncan, OK (US); David Loveless, Houston, TX (US); Nathan Carl Schultheiss, Houston, TX (US); Ali Alwattari, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/433,736

(22) PCT Filed: Feb. 26, 2014

(86) PCT No.: PCT/US2014/018685
§ 371 (c)(1),
(2) Date: Apr. 6, 2015

(87) PCT Pub. No.: WO2014/149468
PCT Pub. Date: Sep. 25, 2014

(65) Prior Publication Data
US 2015/0275251 A1    Oct. 1, 2015

Related U.S. Application Data

(60) Provisional application No. 61/789,200, filed on Mar. 15, 2013.

(51) Int. Cl.
*C12P 19/04*    (2006.01)
*C09K 8/90*    (2006.01)
(Continued)

(52) U.S. Cl.
CPC ............... *C12P 19/04* (2013.01); *C09K 8/035* (2013.01); *C09K 8/08* (2013.01); *C09K 8/68* (2013.01);
(Continued)

(58) Field of Classification Search
None
See application file for complete search history.

(56) References Cited

U.S. PATENT DOCUMENTS 2,854,407 A * 9/1958 Mallory ................. C09K 8/206
                                                    210/730
3,020,206 A * 2/1962 Lindblom ............... C08B 37/00
                                                    106/205.01
(Continued)

FOREIGN PATENT DOCUMENTS

WO       03053158 A2    7/2003
WO     2014149468 A1    9/2014

OTHER PUBLICATIONS

Biochem. Soc. Trans. 20(1):23-26, "Mechanism and Regulation of Galactomannan Biosynthesis in Developing Leguminous Seeds," 1992, ISSN: 0300-5127.
(Continued)

*Primary Examiner* — Angela M DiTrani
*Assistant Examiner* — Anuradha Ahuja
(74) *Attorney, Agent, or Firm* — McDermott Will & Emery LLP; Craig Roddy

(57) ABSTRACT

Methods of biosynthesizing bacterial extracellular galactomannan polysaccharides for use in subterranean formation operations such as drilling operations, fracturing operations, or gravel packing operations including providing a feedstock comprising mannose and galactose; providing bacteria effective at fermenting mannose and galactose; introducing the bacteria to the feedstock; and fermenting the bacteria so (Continued)

as to produce an extracellular galactomannan polysaccharide.

20 Claims, 1 Drawing Sheet

(51) Int. Cl.
    *E21B 43/16* (2006.01)
    *C09K 8/035* (2006.01)
    *C09K 8/68* (2006.01)
    *C09K 8/08* (2006.01)
(52) U.S. Cl.
    CPC ............. *C09K 8/905* (2013.01); *E21B 43/16* (2013.01); *C09K 2208/30* (2013.01)

(56) References Cited

U.S. PATENT DOCUMENTS

| | | | | |
|---|---|---|---|---|
| 3,301,723 A * | 1/1967 | Chrisp | ............ | C08B 37/0087 106/205.71 |
| 3,301,848 A * | 1/1967 | Halleck | ............ | B21D 51/383 106/162.1 |
| 3,933,788 A * | 1/1976 | Kang | ............ | C08B 37/00 435/101 |
| 4,186,025 A * | 1/1980 | Kang | ............ | C12P 19/04 106/125.1 |
| 5,047,332 A * | 9/1991 | Chahal | ............ | A23K 1/007 426/53 |
| 5,130,249 A * | 7/1992 | Hardin | ............ | C09K 8/905 435/101 |
| 5,288,618 A * | 2/1994 | Hardin | ............ | C09K 8/905 435/101 |
| 5,296,245 A * | 3/1994 | Clarke | ............ | A23L 1/052 426/49 |
| 5,480,785 A | 1/1996 | de Troostembergh et al. | | |
| 6,060,436 A | 5/2000 | Snyder et al. | | |
| 6,271,001 B1 * | 8/2001 | Clarke | ............ | A61K 8/73 435/41 |
| 7,265,265 B2 | 9/2007 | Dhugga | | |
| 7,585,818 B2 | 9/2009 | Segura | | |
| 2003/0162300 A1 | 8/2003 | Kunz et al. | | |
| 2005/0075497 A1* | 4/2005 | Utz | ............ | A23L 1/0526 536/114 |
| 2010/0227366 A1* | 9/2010 | Iwai | ............ | A61K 36/74 435/101 |
| 2011/0063270 A1 | 3/2011 | Minami | | |
| 2011/0100631 A1* | 5/2011 | Labeau | ............ | C09K 8/588 166/305.1 |
| 2011/0214868 A1 | 9/2011 | Funkhouser et al. | | |
| 2012/0220503 A1* | 8/2012 | Sanchez Reyes | ...... | C09K 8/685 507/213 |
| 2013/0333888 A1* | 12/2013 | Rincon-Torres | ....... | C09K 8/685 166/279 |
| 2014/0090848 A1* | 4/2014 | Li | ............ | C09K 8/035 166/308.1 |

OTHER PUBLICATIONS

American Society for Microbiology, Applied and Environmental Microbiology, Aug. 1983, vol. 46, No. 2, 392-399.
International Search Report and Written Opinion for PCT/US2014/018685 dated Jun. 25, 2014.

* cited by examiner

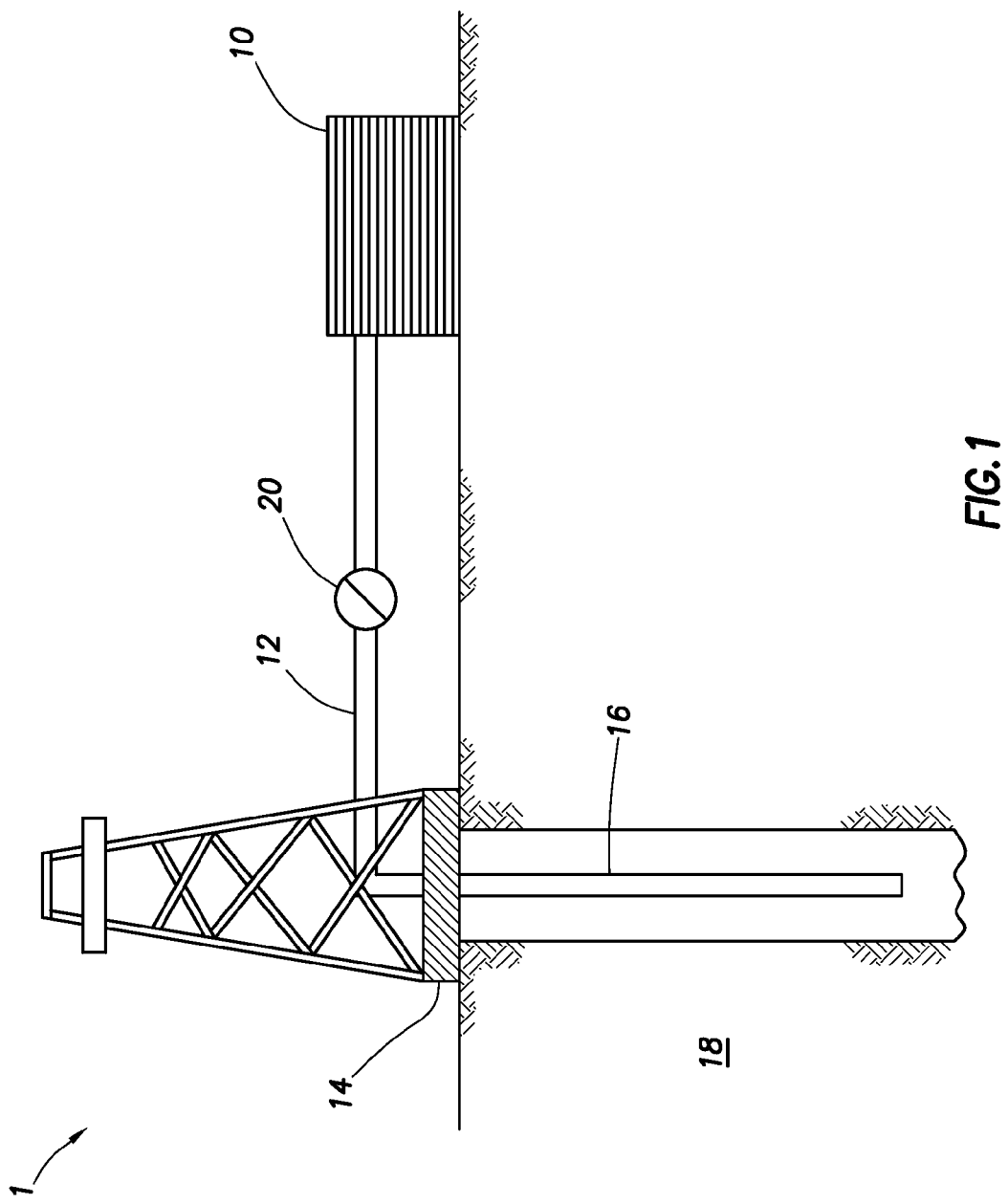

METHODS OF BIOSYNTHESIZING BACTERIAL EXTRACELLULAR GALACTOMANNAN POLYSACCHARIDES AND SUBUNITS THEREOF FOR USE IN SUBTERRANEAN FORMATION OPERATIONS

CROSS-REFERENCE TO RELATED APPLICATIONS

This application claims priority to U.S. Provisional Patent Application Ser. No. 61/789,200, filed on Mar. 15, 2013 entitled "Methods of Biosynthesizing Bacterial Extracellular Galactomannan Polysaccharides for Use in Subterranean Formation Operations."

BACKGROUND

The present disclosure relates to the biosynthesis of bacterial extracellular galactomannan polysaccharides and subunits thereof for use in subterranean formation operations. More particularly, the present disclosure relates to preparation of an extracellular galactomannan polysaccharide derived from mannose and galactose monosaccharides for use in subterranean formation operations.

Treatment fluids may be used in a variety of subterranean formation operations including, drilling operations, stimulation operations, sand control operations, and the like. Subterranean operations often require the use of treatment fluids that are sufficiently viscous to suspend solids, such as drill cuttings, proppant, gravel, and the like. For example, stimulation operations, such as hydraulic fracturing, typically require the use of viscosified treatment fluids in order to maintain proppant suspension for placement in fractures. By keeping the fracture from fully closing, the proppants aid in forming conductive paths to allow produced fluids, such as hydrocarbons, to flow. Similarly, sand control operations typically require the use of viscous treatment fluids to carry gravel particulates downhole to a particular location, usually between a gravel pack screen to prevent the transport of sand or other unconsolidated particles with produced fluids. The gravel particulates create a physical barrier to the transport of the sand or unconsolidated particulates. Failure of the treatment fluid to suspend the gravel particulates (i.e., maintain sufficient viscosity) could result in the deposition of the gravel particulates in an undesired location, thus frustrating the purpose of the treatment fluids.

To obtain the necessary viscosity to carry particulates, gelling agents are commonly used to viscosify treatment fluids. Such gelling agents are generally polymeric materials such as, for example, galactomannans, cellulose derivatives, and biopolymers. Galactomannans, polysaccharides comprised of the monosaccharide subunits mannose and galactose, are often preferred gelling agents because they are relatively inexpensive and exhibit high efficiency and performance in subterranean formation operations because they can be used effectively at relatively low concentrations with crosslinking agents to form high yield point fluids that can support and transport particulates (e.g., cutting particulates, proppant particulates, gravel particulates, and the like). Additionally, they can add sufficient viscosity to provide high flow viscosity fluids that are capable of fracturing oil bearing subterranean formations.

Galactomannans serve as storage carbohydrates that accumulate in the endosperm of seeds of leguminous plants (e.g., fenugreek plants (*Trigonella foenum-graecum*), guar bean plants (*Cyamopsis tetragonoloba*), tara plants (*Caesalpinia spinosa*), locust bean plants (*Ceratonia siliqua*)). Galactomannans are polysaccharides consisting of a (1→4)-linked β-D-mannopyranose backbone with branchpoints from their 6-positions linked to α-D-galactose (1→6)-linked α-D-galactopyranose). Because galactomannans are produced in plants, their supply for use in treatment fluids in subterranean formation operations may be limited by the natural life cycle of the plants and related farming limitations (e.g., seasonal fluctuations, land availability, biological variability, and the like). Their supply may be further limited by global economic conditions and normal supply and demand fluctuations. Therefore, a method of producing commercial quantities of galactommanan for use in subterranean treatment operations that is renewable and season independent may be of benefit to one of ordinary skill in the art.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 1 depicts an embodiment of a system configured for delivering the treatment fluids of the embodiments described herein to a downhole location.

DETAILED DESCRIPTION

The present disclosure relates to the biosynthesis of bacterial extracellular polysaccharides for use in subterranean formation operations. More particularly, the present disclosure relates to preparation of extracellular galactomannan polysaccharides and subunits thereof derived from mannose and galactose monosaccharides. As used herein, the term "extracellular subunit," and any variation thereof (e.g., simply "subunit"), refers to monosaccharides, disaccharides, and/or oligosaccharides that may be reacted or otherwise bonded to form a galactomannan polysaccharide. As used herein, unless otherwise indicated, the term "extracellular galactomannan polysaccharide" encompasses all extracellular subunits that may form a galactomannan polysaccharide, including claim language and any reference to "subunits," in addition to "extracellular galactomannan polysaccharide," and is not intended to indicate that the term "extracellular galactomannan polysaccharide" includes all extracellular subunits, as well. The methods of the present disclosure are useful in manufacturing commercial quantities of galactomannan for use in any subterranean treatment operations requiring viscosified treatment fluids (e.g., drilling fluids, fracturing fluids, gravel packing fluids, and the like). While the extracellular galactomannan polysaccharides of the present disclosure are beneficial to viscosifying fluids, they may also be utilized in any drilling fluid for the purpose of controlling friction forces, as well. Specifically, the extracellular galactomannan polysaccharides of the present disclosure may reduce drag forces of the fluids which they viscosify.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and from time to time. While a developer's efforts might be complex and time-consuming, such efforts would be, nevertheless, a routine undertaking for those of ordinary skill the art having benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

In some embodiments, the present disclosure provides a method of producing an extracellular galactomannan polysaccharide. The extracellular galactomannan polysaccharide may be produced by introducing a bacteria effective at fermenting mannose and galactose to a feedstock comprising a base stock and mannose and galactose. The bacteria ferments the mannose and galactose and produces an extracellular galactomannan polysaccharide and/or subunits thereof. The bacteria used in the methods of the present disclosure may include any bacteria capable of fermenting mannose and galactose, including genetically engineered bacteria whose DNA profile has been modified to allow such bacteria to ferment mannose and galactose. By way of non-limiting example, certain marine bacteria have been identified as capable of fermenting mannose and galactose so as to produce an extracellular galactomannan polysaccharide.

The fermentation process of the present disclosure involves the cultivation of the bacteria on the feedstock described herein. The bacteria increase in number by consuming the nutrients of the feedstock and replicating, while producing the extracellular galactomannan polysaccharides and/or subunits thereof of the present disclosure in their cell walls. For example, in some embodiments, the cultivation of the bacteria on the feedstock may beneficially amplify the amount of extracellular subunits capable of forming galactomannan polysaccharides. As used herein, the term "feedstock" refers to a liquid, gel, or solid substrate composition capable of supporting the growth of bacteria. In some embodiments, the feedstock may be composed of a carbon source, water, and a salt source. In some embodiments, the feedstock may further comprise mannose and galactose therein.

The carbon source in the feedstock provides a food source for the bacteria, which are capable of breaking down the carbon source into simple sugars, lipids, DNA, and proteins that can be utilized in metabolic processes. Suitable carbon sources for use in the feedstock may include, but are not limited to, glucose; succinate; a starch; a maltodextrin; maltose; a peptone; a tryptone; and any combination thereof. In some embodiments, the carbon source is present in the feedstock in the range of between about 0.1% to about 50% by volume of the feedstock, and preferably in the range of between about 0.3% to about 20% by volume of the feedstock. The carbon source is preferably in the feedstock such that the final dry weight of the bacteria after fermentation is comprised of the carbon source in an amount of about 50%.

Suitable water sources for use in the feedstock of the present disclosure include distilled water; deionized water; sterile water; seawater; brine; and any combination thereof. In preferred embodiments, the water source is distilled water; deionized water; sterile water; and any combination thereof, being sufficiently free of solid particulates. The water source chosen should be capable of solubilizing the additives placed therein (e.g., the carbon source and the salt source).

The salt source for use in the feedstock of the present disclosure permits the bacteria to perform protein and nucleic acid synthesis, and provides osmotic pressure balance in the feedstock. Suitable salt sources may include, but are not limited to, magnesium; nitrogen; phosphorous; sulfur; sodium chloride; yeast extract; beef extract; and any combination thereof. In some embodiments, the base stock may comprise tryptone, yeast extract, and sodium chloride. In some embodiments, the salt source is present in the feedstock in the range of between about 0.001% to about 10% by volume of the feedstock, and preferably in the range of between about 0.1 to about 5% by volume of the feedstock. The amount of the salt source to be included in the feedstock of the present disclosure may be determined so as to increase water activity and promote bacterial growth. As used herein, the term "water activity" refers to a measure of how efficiently water may participate in a chemical reaction. Generally, the bacteria effective at fermenting mannose and galactose of the present disclosure should be grown in a feedstock having a water activity in the range of about 0.75 to about 1. One of ordinary skill in the art, with the benefit of this disclosure, will recognize the amount of the salt source to include in the feedstock of the present disclosure based on factors including, but not limited to, the type of water source used, the temperature of the feedstock, the type of salt source used, the type of bacteria used, and the like.

The feedstock of the present disclosure is typically liquid, but may be mixed with agar to form a gelled media (e.g., for use in a petri dish). Therefore, the bacteria of the present disclosure may be fermented either in suspension in a liquid feedstock or in a gelled feedstock. In some embodiments, the feedstock may further comprise a buffer (e.g. a TRIS buffer, glycylglycine, sodium bicarbonate, and the like). The buffer may control the pH of the feedstock in order to provide a stable growth media for the bacteria. In those embodiments where a buffer is included in the feedstock, one of ordinary skill in the art, with the benefit of this disclosure, will understand the appropriate amount to include to achieve desired pH results. Other known additives may be included in the feedstock to enhance growth of the bacteria described herein or ease handling requirements as long as the additives do not interfere with the production of the extracellular galactomannan polysaccharide of the present disclosure.

In some embodiments of the present disclosure, mannose and galactose may be added to feedstock (with or without additional additives). In some embodiments, the mannose and galactose may replace some or all of the carbon source component in the feedstock, as both qualify as an energy-supplying carbon source. This may beneficially promote an increase in the yield of extracellular galactomannan polysaccharides. In some embodiments, the combined mannose and galactose represent the carbon source in the range of from about 30% to about 95%, the remainder being supplied by a different carbon source. In other embodiments, the combined mannose and galactose represent the carbon source in the range of from about 40% to about 90%, the remainder being supplied by a different carbon source. In still other embodiments, the combined mannose and galactose may be present in the feedstock in an amount of from about 0.1 to about 10% by volume of the feedstock, irrespective of the carbon source.

Typically, the feedstock of the present disclosure is sterilized by autoclaving after the addition of mannose and galactose, but prior to introducing bacteria effective at fermenting mannose and galactose to it. By way of non-limiting example, the feedstock may be autoclaved at 121° C. for 15-20 minutes.

The ratio of mannose to galactose may be manipulated in order to induce the bacteria during fermentation to produce variants of extracellular galactomannan polysaccharides and/or subunits thereof, which may vary in their ability to viscosify treatment fluids for use in subterranean formation operations. In some embodiments, the mannose and galactose is present in the feedstock in a ratio of about 1:1 and the produced extracellular galactomannan polysaccharide is a fenugreek gum. In other embodiments, the mannose and galactose is present in the feedstock in a ratio of about 2:1 and the produced extracellular galactomannan polysaccharide is a guar gum. In still other embodiments, the mannose and galactose is present in the feedstock in a ratio of about 3:1 and the produced extracellular galactomannan polysaccharide is a tara gum. In yet other embodiments, the mannose and galactose is present in the feedstock in a ratio of about 4:1 and the produced extracellular galactomannan polysaccharide is a locust bean gum. An advantage of the methods of the present disclosure is that where one ratio of mannose and galactose is provided in the feedstock, the natural variation of uptake by the bacteria may result in an unbalanced fermentation such that any of the galactomannan variants may be produced as extracellular polysaccharides, monosaccharides, disaccharides, and/or oligosaccharides that may be used in subterranean formation operational treatment fluids.

In some embodiments, the present disclosure provides a method of purifying the extracellular galactomannan polysaccharides and/or subunits thereof of the present disclosure. Unwanted proteins and nucleic acids are first precipitated and separated from the bacteria, followed by precipitation and isolation of the extracellular galactomannan polysaccharide and/or subunits thereof. The purification of the extracellular galactomannan polysaccharide may be performed by any method known in the art including, for example, commercially available protein purification kits. In some embodiments, for example, the purification may utilize RNAse, DNAse, or protease to remove contamination with bacterial nucleic acids and proteins.

In some embodiments, the purification may include a diafiltration step (e.g., by tangential flow diafiltration) after the unwanted proteins and nucleic acids are precipitated and removed but prior to precipitation and isolation of the extracellular galactomannan polysaccharide and/or subunits thereof. As defined herein, the term "diafiltration" refers to the use of ultrafiltration membranes to remove salts or other microsolutes from a solution. In some embodiments, the purified extracellular galactomannan polysaccharides and/or subunits thereof may be further decontaminated by known methods in the art (e.g., by centrifugation in an alcohol). In some embodiments, the purified subunits may be reacted or otherwise bonded together to form galactomannan polysaccharides for use in the embodiments described herein.

In some embodiments, the extracellular galactomannan polysaccharides and/or subunits thereof of the present disclosure may be introduced into a treatment fluid for use in a subterranean formation operation after purification. In some embodiments, the extracellular subunits may be capable of reacting or otherwise bonding in the treatment fluid to form galactomannan polysaccharides. In some embodiments, the purified extracellular galactomannan polysaccharides of the present disclosure may be present in the treatment fluid in an amount in the range of about 0.1% to about 80% by weight of the treatment fluid.

In other embodiments, the fermented bacteria having produced the extracellular galactomannan polysaccharides of the present disclosure may themselves be introduced into a treatment fluid for use in a subterranean formation operation without a purification step. This method may be preferred when time constraints are placed on a particular subterranean operation. In those embodiments where the bacteria is directly added to the treatment fluid, the bacteria may be present in an amount equivalent to produce purified extracellular galactomannan polysaccharide in an amount in the range of from about 0.1% to about 30% by weight of the treatment fluid. In other embodiments where the bacteria is directly added to the treatment fluid, the bacteria may be present in an amount equivalent to produce purified extracellular galactomannan polysaccharide in an amount in the range of from about 0.2% to about 60% by weight of the treatment fluid. That is, the bacteria may be present in an amount of up to about 50% greater than the range of equivalent purified extracellular galactomannan polysaccharide to be added to the treatment fluid. This may be preferred so as to ensure proper viscosification of the treatment fluid. Factors that may affect the amount of bacteria to be added to the treatment fluid may include, but are not limited to, temperature, pressure, downhole conditions, and the like. One of ordinary skill in the art, with the benefit of this disclosure, will recognize the appropriate amount of bacteria to include in the treatment fluids to achieve a particular result.

The treatment fluid may be a drilling fluid, a fracturing fluid, a gravel packing fluid, or any other treatment fluid that requires viscosification. The treatment fluids of the present disclosure comprise an aqueous base fluid and may be used to resolubilize isolated and purified extracellular galactomannan polysaccharides and/or subunits thereof, for example. Suitable aqueous base fluids for use in the treatment fluids of the present disclosure may comprise fresh water; saltwater (e.g., water containing one or more salts dissolved therein); brine (e.g., saturated salt water); seawater; or combinations thereof. Generally, the water may be from any source, provided that it does not contain components that might adversely affect the stability and/or performance of the treatment fluids comprising the extracellular galactomannan polysaccharides of the present disclosure. In certain embodiments, the viscosity of the aqueous base fluid can be adjusted, among other purposes, to provide additional particulate transport and suspension in the treatment fluids used in the methods of the present disclosure. In certain embodiments, the pH of the aqueous base fluid may be adjusted (e.g., by a buffer or other pH adjusting agent), to adjust the viscosity. One of ordinary skill in the art, with the benefit of this disclosure, will recognize when such viscosity and/or pH adjustments are appropriate. In some embodiments, the pH range may preferably be from about 4 to about 11.

In some embodiments, the treatment fluid may further comprise a crosslinking agent capable of interacting with the extracellular galactomannan polysaccharides of the present disclosure, so as to enhance the viscosity of the treatment fluid. Examples of suitable crosslinking agents include, but are not limited to, borate ions; magnesium ions; zirconium IV ions; titanium IV ions; aluminum ions; antimony ions; chromium ions; iron ions; copper ions; magnesium ions; zinc ions; and any combination thereof. These ions may be provided by providing any compound that is capable of producing one or more of these ions. Examples of such compounds include, but are not limited to, ferric chloride; boric acid; disodium octaborate tetrahydrate; sodium diborate; pentaborates; ulexite; colemanite; magnesium oxide; zirconium lactate; zirconium triethanol amine; zirconium lactate triethanolamine; zirconium carbonate; zirconium acetylacetonate; zirconium malate; zirconium citrate; zirconium diisopropylamine lactate; zirconium glycolate; zirconium triethanol amine glycolate; zirconium lactate glycolate; titanium lactate; titanium malate; titanium citrate; titanium ammonium lactate; titanium triethanolamine; titanium acetylacetonate; aluminum lactate; aluminum citrate; an antimony compound; a chromium compound; an iron compound; a copper compound; a zinc compound; and any combination thereof. In certain embodiments of the present disclosure, the crosslinking agent may be formulated to remain inactive until it is "activated" by, among other things, certain conditions in the treatment fluid (e.g., pH, temperature, etc.) and/or interaction with some other substance.

When included, suitable crosslinking agents may be present in the treatment fluids useful in the methods of the present disclosure in an amount sufficient to provide the desired degree of crosslinking between molecules of the extracellular galactomannan polysaccharides. In certain embodiments, the crosslinking agent may be present in the treatment fluids of the present disclosure in an amount in the range of from about 0.005% to about 1% by weight of the treatment fluid. In certain embodiments, the crosslinking agent may be present in the treatment fluids of the present disclosure in an amount in the range of from about 0.05% to about 1% by weight of the treatment fluid. One of ordinary skill in the art, with the benefit of this disclosure, will recognize the appropriate amount of crosslinking agent to include in a treatment fluid of the present disclosure based on, among other things, the temperature conditions of a particular application, the desired degree of viscosification, and/or the pH of the treatment fluid.

The treatment fluids of the present disclosure may further comprise an additive suited to the particular subterranean formation operation for which the treatment fluid is to be used. Suitable additives include, but are not limited to, a salt; a weighting agent; an inert solid; a fluid loss control agent; a corrosion inhibitor; a gelling agent; a surfactant; a particulate; a proppant; a gravel particulate; a lost circulation material; a foaming agent; a gas; a pH control additive; a breaker; a biocide; a stabilizer; a scale inhibitor; a friction reducer; a clay stabilizing agent; and any combination thereof.

In various embodiments, systems configured for delivering the treatment fluids (i.e., the temporary sealant slurry and the fracturing fluid) described herein to a downhole location are described. In various embodiments, the systems can comprise a pump fluidly coupled to a tubular, the tubular containing the treatment fluids described herein. It will be appreciated that while the system described below may be used for delivering either or both of the temporary sealant slurry and the fracturing fluid, each treatment fluid is delivered separately into the subterranean formation.

The pump may be a high pressure pump in some embodiments. As used herein, the term "high pressure pump" will refer to a pump that is capable of delivering a fluid downhole at a pressure of about 1000 psi or greater. A high pressure pump may be used when it is desired to introduce the treatment fluids to a subterranean formation at or above a fracture gradient of the subterranean formation, but it may also be used in cases where fracturing is not desired. In some embodiments, the high pressure pump may be capable of fluidly conveying particulate matter, such as the non-degradable particulates, the degradable particulates, and the proppant particulates described in some embodiments herein, into the subterranean formation. Suitable high pressure pumps will be known to one having ordinary skill in the art and may include, but are not limited to, floating piston pumps and positive displacement pumps.

In other embodiments, the pump may be a low pressure pump. As used herein, the term "low pressure pump" will refer to a pump that operates at a pressure of about 1000 psi or less. In some embodiments, a low pressure pump may be fluidly coupled to a high pressure pump that is fluidly coupled to the tubular. That is, in such embodiments, the low pressure pump may be configured to convey the treatment fluids to the high pressure pump. In such embodiments, the low pressure pump may "step up" the pressure of the treatment fluids before reaching the high pressure pump.

In some embodiments, the systems described herein can further comprise a mixing tank that is upstream of the pump and in which the treatment fluids are formulated. In various embodiments, the pump (e.g., a low pressure pump, a high pressure pump, or a combination thereof) may convey the treatment fluids from the mixing tank or other source of the treatment fluids to the tubular. In other embodiments, however, the treatment fluids may be formulated offsite and transported to a worksite, in which case the treatment fluid may be introduced to the tubular via the pump directly from its shipping container (e.g., a truck, a railcar, a barge, or the like) or from a transport pipeline. In either case, the treatment fluids may be drawn into the pump, elevated to an appropriate pressure, and then introduced into the tubular for delivery downhole.

FIG. 1 shows an illustrative schematic of a system that can deliver the treatment fluids of the present disclosure to a downhole location, according to one or more embodiments. It should be noted that while FIG. 1 generally depicts a land-based system, it is to be recognized that like systems may be operated in subsea locations as well. As depicted in FIG. 1, system 1 may include mixing tank 10, in which the treatment fluids of the embodiments herein may be formulated. The treatment fluids may be conveyed via line 12 to wellhead 14, where the treatment fluids enter tubular 16, tubular 16 extending from wellhead 14 into subterranean formation 18. Upon being ejected from tubular 16, the treatment fluids may subsequently penetrate into subterranean formation 18. Pump 20 may be configured to raise the pressure of the treatment fluids to a desired degree before introduction into tubular 16. It is to be recognized that system 1 is merely exemplary in nature and various additional components may be present that have not necessarily been depicted in FIG. 1 in the interest of clarity. Non-limiting additional components that may be present include, but are not limited to, supply hoppers, valves, condensers, adapters, joints, gauges, sensors, compressors, pressure controllers, pressure sensors, flow rate controllers, flow rate sensors, temperature sensors, and the like.

Although not depicted in FIG. 1, the treatment fluid may, in some embodiments, flow back to wellhead 14 and exit subterranean formation 18. In some embodiments, the treatment fluid that has flowed back to wellhead 14 may subsequently be recovered and recirculated to subterranean formation 18.

It is also to be recognized that the disclosed treatment fluids may also directly or indirectly affect the various downhole equipment and tools that may come into contact with the treatment fluids during operation. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIG. 1.

Thus, some embodiments of the present disclosure provide:

A. A method comprising: providing a feedstock, wherein the feedstock further comprises mannose and galactose; providing bacteria effective at fermenting mannose and galactose; introducing the bacteria to the feedstock; and fermenting the bacteria so as to produce an extracellular galactomannan polysaccharide.

B. A method comprising: providing an extracellular galactomannan polysaccharide, wherein the extracellular polysaccharide is formed by the fermenting bacteria effective at fermenting mannose and galactose in the presence of a feedstock, wherein the feedstock further comprises mannose and galactose; and preparing a treatment fluid comprising an aqueous base fluid and the extracellular galactomannan polysaccharide; and introducing the treatment fluid into a subterranean formation.

C. A method comprising: preparing a treatment fluid comprising an aqueous base fluid and an extracellular galactomannan polysaccharide, wherein the extracellular galactomannan polysaccharide is formed by the fermenting bacteria effective at fermenting mannose and galactose in the presence of a feedstock, wherein the feedstock further comprises mannose and galactose, and wherein the extracellular polysaccharide is purified; and introducing the treatment fluid into a subterranean formation.

Each of embodiments A, B, and C (above) may have one or more of the following additional elements in any combination:

Element 1: A method wherein the mannose and galactose are present in the feedstock in a ratio of about 1:1 such that at least a portion of the extracellular galactomannan polysaccharide comprises a fenugreek gum.

Element 2: A method wherein the mannose and galactose are present in the feedstock in a ratio of about 2:1 such that at least a portion of the extracellular galactomannan polysaccharide comprises a guar gum.

Element 3: A method wherein the mannose and galactose are present in the feedstock in a ratio of about 3:1 such that at least a portion of the extracellular galactomannan polysaccharide comprises a tara gum.

Element 4: A method wherein the mannose and galactose are present in the feedstock in a ratio of about 4:1 such that at least a portion of the extracellular galactomannan polysaccharide comprises a locust bean gum.

Element 5: A method further comprising the step of purifying the extracellular galactomannan polysaccharide.

Element 6: A method further comprising preparing a treatment fluid comprising an aqueous base fluid and the extracellular galactomannan polysaccharide, and introducing the treatment fluid into a subterranean formation.

Element 7: A method wherein the treatment fluid is used in a drilling operation, a fracturing operation, or a gravel packing operation.

Element 8: A method wherein the treatment fluid further comprises a crosslinking agent.

Element 9: A method wherein the treatment fluid further comprises an additive selected from the group consisting of a salt; a weighting agent; an inert solid; a fluid loss control agent; a corrosion inhibitor; a gelling agent; a surfactant; a particulate; a proppant; a gravel particulate; a lost circulation material; a foaming agent; a gas; a pH control additive; a breaker; a biocide; a stabilizer; a scale inhibitor; a friction reducer; a clay stabilizing agent; and any combination thereof.

Element 10: Further comprising a wellhead with a tubular extending therefrom and into the subterranean formation and a pump coupled to the tubular, wherein the step of: introducing the treatment fluid into the subterranean formation comprises introducing the treatment fluid the tubular.

While any of the above combinations is specifically contemplated herein, some non-limiting examples of suitable combinations include: A with 1, 5, 6, and 9; B with 3, 8 and 9; B with 7 and 10; C with 4 and 9; C with 2 and 10.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
   providing a feedstock comprising a carbon source in an amount of about 10% to about 50% by volume of the feedstock and having a water activity of about 0.75 to about 1, wherein the feedstock further comprises mannose and galactose;
   providing bacteria capable of fermenting mannose and galactose, wherein the mannose and galactose combined are present in the feedstock in an amount of about 0.1% to about 10% by volume of the feedstock;
   introducing the bacteria to the feedstock; and
   fermenting the feedstock so as to produce an extracellular galactomannan polysaccharide,
   wherein about 50% of a dry weight of the bacteria after fermentation comprises the carbon source.

2. The method of claim 1, wherein the mannose and galactose are present in the feedstock in a ratio of about 1:1 such that at least a portion of the extracellular galactomannan polysaccharide comprises a fenugreek gum.

3. The method of claim 1, wherein the mannose and galactose are present in the feedstock in a ratio of about 2:1 such that at least a portion of the extracellular galactomannan polysaccharide comprises a guar gum.

4. The method of claim 1, wherein the mannose and galactose are present in the feedstock in a ratio of about 3:1 such that at least a portion of the extracellular galactomannan polysaccharide comprises a tara gum.

5. The method of claim 1, wherein the mannose and galactose are present in the feedstock in a ratio of about 4:1 such that at least a portion of the extracellular galactomannan polysaccharide comprises a locust bean gum.

6. The method of claim 1, further comprising purifying the extracellular galactomannan polysaccharide.

7. The method of claim 1, further comprising preparing a treatment fluid comprising an aqueous base fluid, the extracellular galactomannan polysaccharide, and the bacteria after fermentation, and introducing the treatment fluid into a subterranean formation.

8. A method comprising:
   providing an extracellular galactomannan polysaccharide, wherein the extracellular galactomannan polysaccharide is formed by bacteria fermenting a feedstock comprising a carbon source in an amount of about 10% to about 50% by volume of the feedstock, mannose, and galactose,
   wherein the feedstock has a water activity of about 0.75 to about 1,
   wherein about 50% of a dry weight of the bacteria after fermentation comprises the carbon source, and
   wherein the mannose and galactose combined are present in the feedstock in an amount of about 0.1% to about 10% by volume of the feedstock; and
   preparing a treatment fluid comprising an aqueous base fluid and the extracellular galactomannan polysaccharide; and
   introducing the treatment fluid into a subterranean formation.

9. The method of claim 8, wherein the mannose and galactose are present in the feedstock in a ratio of about 1:1 such that at least a portion of the extracellular galactomannan polysaccharide comprises a fenugreek gum.

10. The method of claim 8, wherein the mannose and galactose are present in the feedstock in a ratio of about 2:1 such that at least a portion of the extracellular galactomannan polysaccharide comprises a guar gum.

11. The method of claim 8, wherein the mannose and galactose are present in the feedstock in a ratio of about 3:1 such that at least a portion of the extracellular galactomannan polysaccharide comprises a tara gum.

12. The method of claim 8, wherein the mannose and galactose are present in the feedstock in a ratio of about 4:1 such that at least a portion of the extracellular galactomannan polysaccharide comprises a locust bean gum.

13. The method of claim 8, further comprising purifying the extracellular galactomannan polysaccharide prior to the step of preparing the treatment fluid.

14. The method of claim 8, further comprising a wellhead with a tubular extending therefrom and into the subterranean formation and a pump coupled to the tubular, wherein the step of introducing the treatment fluid into the subterranean formation comprises introducing the treatment fluid into the tubular.

15. A method comprising:
   preparing a treatment fluid comprising an aqueous base fluid and an extracellular galactomannan polysaccharide,
   wherein the extracellular galactomannan polysaccharide is formed by bacteria fermenting a feedstock comprising a carbon source in an amount of about 10% to about 50% by volume of the feedstock, mannose, and galactose,
   wherein the feedstock has a water activity of about 0.75 to about 1,
   wherein about 50% of a dry weight of the bacteria after fermentation comprises the carbon source,
   wherein the extracellular polysaccharide is purified, and
   wherein the mannose and galactose combined are present in the feedstock in an amount of about 0.1% to about 10% by volume of the feedstock; and
   introducing the treatment fluid into a subterranean formation.

16. The method of claim 15, wherein the mannose and galactose are present in the feedstock in a ratio of about 1:1 such that at least a portion of the extracellular galactomannan polysaccharide comprises a fenugreek gum.

17. The method of claim 15, wherein the mannose and galactose are present in the feedstock in a ratio of about 2:1 such that at least a portion of the extracellular galactomannan polysaccharide comprises a guar gum.

18. The method of claim 15, wherein the mannose and galactose are present in the feedstock in a ratio of about 3:1 such that at least a portion of the extracellular galactomannan polysaccharide comprises a tara gum.

19. The method of claim 15, wherein the mannose and galactose are present in the feedstock in a ratio of about 4:1 such that at least a portion of the extracellular galactomannan polysaccharide comprises a locust bean gum.

20. The method of claim 15, further comprising a wellhead with a tubular extending therefrom and into the subterranean formation and a pump coupled to the tubular, wherein the step of introducing the treatment fluid into the subterranean formation comprises introducing the treatment fluid into the tubular.

* * * * *